United States Patent [19]

Rosenheimer

[11] Patent Number: 5,497,771
[45] Date of Patent: Mar. 12, 1996

[54] APPARATUS FOR MEASURING THE OXYGEN SATURATION OF FETUSES DURING CHILDBIRTH

[75] Inventor: Michael N. Rosenheimer, Guenzlhofen, Germany

[73] Assignee: MIPM Mammendorfer Institut fuer Physik und Medizin GmbH, Hattenhofen, Germany

[21] Appl. No.: 221,186

[22] Filed: Mar. 30, 1994

[30] Foreign Application Priority Data

Apr. 2, 1993 [DE] Germany ............... 43 10 929.2
Mar. 7, 1994 [DE] Germany ............... 44 07 541.3

[51] Int. Cl.$^6$ ..................................... A61B 5/00
[52] U.S. Cl. ..................... 128/633; 128/634; 128/643
[58] Field of Search ..................... 128/633–634, 128/639, 642–643, 664–665, 670

[56] References Cited

U.S. PATENT DOCUMENTS 4,913,151  4/1990  Harui et al. ............... 128/634
5,154,175  10/1992  Gunther ..................... 128/633
5,345,935  9/1994  Hirsch et al. ............. 128/633 X

FOREIGN PATENT DOCUMENTS 9115151  10/1991  WIPO ..................... 128/634
9118549  12/1991  WIPO ..................... 128/634

Primary Examiner—Angela D. Sykes
Attorney, Agent, or Firm—McAulay Fisher Nissen Goldberg & Kiel

[57] ABSTRACT

An apparatus for measuring the oxygen saturation of fetuses during childbirth, using a probe, assigned to the fetal scalp, with two or four photodiodes operating at different wave lengths and a photodetector disposed in the plane of the photodiodes as parts of an optical reflection measurement portion for determining the oxygen saturation in the arterial or pulsating bloodstream, which is proportional to the ratio of oxyhemoglobin to the sum of oxyhemoglobin and desoxyhemoglobin by reflection measurement in an area, which is not subjected to a partial vacuum. Output signals of the apparatus are supplied to an evaluating pulsoxymeter over a cable connection having a plug-and-socket connector.

11 Claims, 2 Drawing Sheets

5,497,771

APPARATUS FOR MEASURING THE OXYGEN SATURATION OF FETUSES DURING CHILDBIRTH

BACKGROUND OF THE INVENTION a) Field of the Invention

The invention relates to an apparatus for measuring the oxygen saturation of fetuses during childbirth, using a probe, which is assigned to the fetal scalp and held in position by means of a partial vacuum and has two photodiodes operating at different wavelengths and a photodetector as parts of an optical reflection measurement portion for determining the oxygen saturation in the arterial or pulsating bloodstream of fetuses, which is proportional to the ratio of oxyhemoglobin to the sum of oxyhemoglobin and desoxyhemoglobin, the output signals of the probe being supplied to an evaluating pulsoxymeter over a lead connection having a plug-and-socket connector.

b) Background Art

In a known apparatus of this type, as disclosed in EP-O-135 840 A2, a probe, which comprises two photodiodes operating at different wavelengths and one photodetector, is held fast by a partial vacuum at a fetal scalp in order to measure the oxygen saturation that is proportional to the ratio of oxyhemoglobin to the sum of oxyhemoglobin and desoxyhemoglobin in the arterial or pulsating bloodstream continuously over the optical reflection measurement portion. For this embodiment of the probe, the photodiodes are disposed in the upper part of the housing and emit light with a frequency of 660 nm (red) and 940 ng (infrared) onto the fetal scalp. The light reflected from the fetal scalp reaches the photodetector, which is disposed in the lower part of the housing and the signals of which are passed on to the pulsoxymeter. This pulsoxymeter evaluates the data so obtained, so that changes in the oxygen saturation in the fetal scalp can be recognized and appropriate medical diagnoses made with the help of the data obtained by the pulsoxymeter and appropriate interventions carried out. Moreover, parts of the housing of the probe are constructed as EKG contact electrodes, one of which, when positioned appropriately, is in contact with the fetal scalp in order to be able to measure, in addition, the fetal heart rate continuously.

Since the partial vacuum region of the known probe extends over the whole of the cross sectional area of the probe, the measurement is also carried out in this partial vacuum region.

As a result, considerable errors can arise during the childbirth process in the measurement of oxygen at fetal scalps, since the oxygen content of the fetal blood at the measuring site decreases appreciably in comparison to the actual oxygen content, due to the local, partial vacuum existing at the measuring site; the partial vacuum thus affects the blood circulation at the measuring site significantly. These measurement errors lead to wrong medical diagnoses and to unnecessary interventions during the delivery process.

The photodiode above the photodetector furthermore leads to a size relationship - probe diameter to length - which makes it difficult to place the probe at the fetal scalp, so that, despite appropriate training and experience, the probe frequently is deposited wrongly or insufficiently, which also leads to major malfunctions and appreciable measurement errors.

Moreover, as a result of the arrangement of the photodiode and photodetector in superimposed planes above the measurement site, there are light diffractions and undesirable light reflections and, with that, a poorly illuminated measurement area. These effects are intensified if the probe is placed inaccurately.

There is therefore a great need to be able to carry out the measurements very accurately and free of mistakes, in order to be able to counteract any brain damage, which may occur in babies due to a lack of oxygen during problem deliveries, in a timely fashion.

OBJECTS AND SUMMARY OF THE INVENTION

It is therefore an object of the invention to develop the known probe further in such a manner that the negative effect of the partial vacuum at the measurement site is avoided, that the spatial extent of the probe is decreased and that, by an extension of the optical measurement portion, the illumination of the measurement site is increased and, with that, an overall improvement in the measurement results is attained, in order to achieve reliable and artifact-free measurements.

Starting out from an apparatus of the initially described type, this inventive objective is accomplished by having the optical reflection measurement portion assigned to a distal emergence planar surface, in which there is no partial vacuum.

Pursuant to a preferred embodiment of the invention, a covering hood, enclosing the distal emergence planar surface, is assigned to the distal emergence planar surface of the probe. The covering hood has a cavity, which is approximately semi-cylindrical in cross section and is assigned to the scalp of the fetus and the circular supporting surfaces of which lie outside of the distal emergence planar surface of the optical reflection measurement portion and surround the probe circularly.

According to a further distinguishing feature of the invention, several (at least two) photodiodes of the optical reflection measurement portion lie on a common planar element with the photodetector and are disposed opposite to one another on a common axis of symmetry assigned to the probe.

Due to the inventive construction of the partial vacuum site and the improvement in the optical reflection measurement portion within the cavity surrounding this site, errors in measurement are largely avoided, since there is no partial vacuum at the measuring site distorting the measurement and since the measurement area is illuminated better than it was previously. Moreover, the handling of the inventive probe is simplified significantly and is more comfortable than previously constructed for all participants since, as a result of the inventive arrangement and construction of the optical measurement portion and the covering hood, the size relationship of diameter to depth can be kept small and, moreover, does not exceed 3:1. The use of a cylindrical tube or other cross sectional shapes for this component as an EKG lead, which serves at the same time as electrical and optical shielding, leads to a significantly smaller construction. A continuous monitoring of the heart rate and of the oxygen content of the arterial or pulsating bloodstream of the fetus can now be carried out without problem at the fetal scalp.

The inventive construction enables the probe to be disposed stably and without slipping at the fetal scalp and the circular construction of the cavity around the optical reflection measurement portion and the smaller dimensions of the probe make it possible to avoid measurement inaccuracies.

Finally, due to the inventive arrangement of the photodiodes on the same planar element as the photodetector, the illumination of the measurement area is increased appreciably; there is no undesirable formation of shadows at the measurement site, since the light path of the emitted light in the optical measurement portion falls on the measuring site without being impeded and is reflected from there.

BRIEF DESCRIPTION OF THE DRAWINGS

The invention is described in the following by means of two embodiments, which are shown diagrammatically in the drawings in which.

DESCRIPTION OF THE PREFERRED EMBODIMENTS

Figure 1:
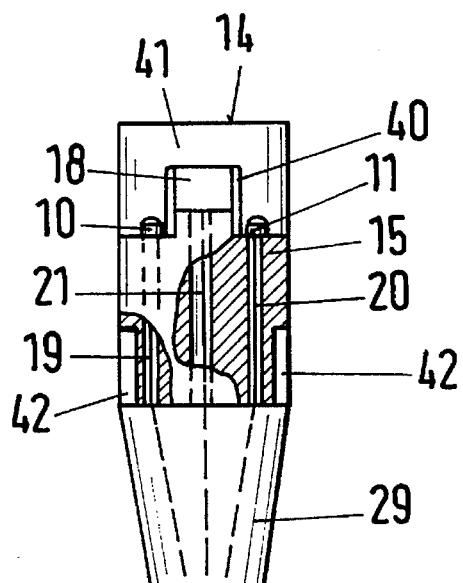
FIG. 1 is an enlarged representation of an inventive apparatus according to a first embodiment with an optical reflection measurement portion comprising two photodiodes and one photodetector of a probe for measuring the oxygen saturation of fetuses during childbirth.
Figure 2:
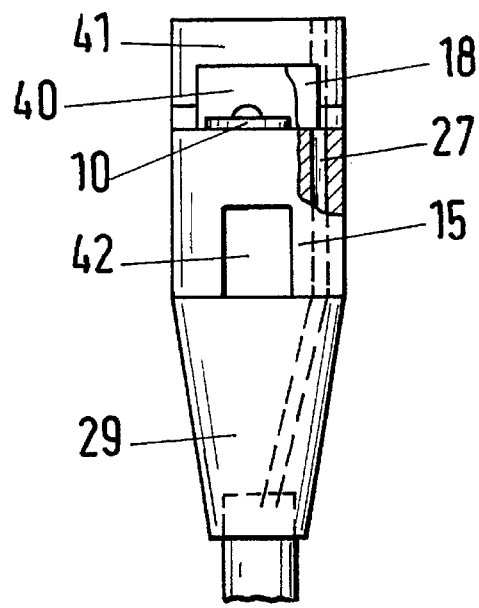
FIG. 2 shows a side view of the probe of FIG. 1.

To measure the oxygen saturation by spectrophotometry of the hemoglobin as shown in FIG. 1, a pulse synchronized, alternating light is generated at wave lengths of 660 nm (red) and 940 nm (infrared) each over a photodiode 10 and 11, which are disposed on opposite sides of a probe 15 and fastened on their inactive surfaces on a common planar element 9 of the probe 15, which has a circular cross section.

With respect to a distal emergence planar surface 14 of the probe 15, which is identical with the measuring site (fetal scalp 3) during the measurement of the oxygen saturation, the angle of emergence of the light beams emitted by the photodiodes is about 90°.

A photodetector 18, the inactive surface of which is fastened on the common planar element 9 of the photodiodes 10 and 11, is assigned to and disposed between these photodiodes 10 and 11. The distance between the active surface of the photodetector 18 and the distal emergence planar surface 14 of the probe 15 is less than the distance between the active surfaces of the photodiodes 10 and 11 and the distal emergence planar surface 14 of the probe 15.

Figure 3:
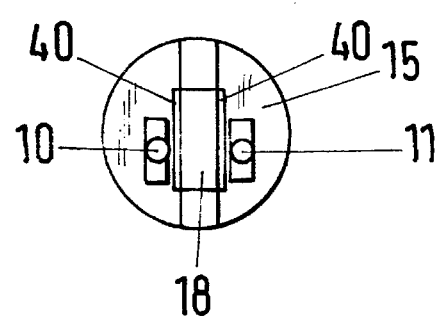
FIG. 3 shows a plan view of the probe of FIG. 1.

As shown in FIGS. 1 and 3, opaque barriers 40 are disposed on either side of the photodetector 18, so that the measurement of the oxygen saturation cannot be distorted by light, which is emitted by the photodiodes 10 and 11, but not reflected directly from the fetal scalp 3.

Furthermore, after the photoelectric parts 10, 11 and 18 are installed, a cover 41 of a silicone casting compound having the same diameter as the probe 15 is applied.

The photodiodes and the photodetector are electrically connected by cable connectors 19, 20 and 21 with a so-called pulsoxymeter 24, the construction of which for the generation and evaluation of the light pulses is not described and not shown here, since it is not part of the invention. The cable connectors 19, 20, 21 are constructed semi-elastically.

As furthermore shown in FIG. 1, a plug-and-socket connector 36 is provided between the probe 15 and the pulsoxymeter 24, in order to be able to sterilize the probe 15 after use.

Mutually opposite recesses 42 are provided on either side of the probe, so that the latter may be placed conveniently with the help of so-called surgical forceps.

The proximal end of the probe has a conically shaped covering hood 29, which tightly surrounds the electrical leads 19, 20 and 21, as well as a suction line 27. A cavity, which is formed between the cover 41 and the cuff of equal diameter (not shown) at the distal end of the probe 15 and the fetal scalp 3, is generated over the suction line 27.

Finally, an equalizing outlet 33 (FIG. 1) is provided, which can be inserted in the cable connectors 19, 20, 21 by way of a plug-and-socket connection 36, in order to be able to electrically adapt the probe 15 optimally to the evaluating unit, namely, the pulsoxymeter 24. The equalizing outlet 33 is an electrical circuit, which matches the light intensities of the photodiodes 10, 11. When the above-described probe 15 is placed on the fetal scalp 3, the percentage oxygen saturation is measured in a known manner and indicated on the pulsoxymeter 24.

According to a second embodiment of the probe 15, for which the same reference numbers have been used for identical components, four photodiodes 10, 11, 12, 13 and one photodetector 18 are assigned to the common planar element 9. The center of the photodetector 18 is identical with the probe center, which is formed by two mutually perpendicular axes of symmetry 7, 8 of the circular probe 15. In this embodiment, the photodiodes 10, 11, 12, 13 are disposed in pairs, mutually opposite to one another, on an imaginary circular path. The axis of symmetry of the photodiodes 10, 11, 12, 13 assigned to the side of smaller dimensions, is identical with an axis of symmetry 7 or 8 of the probe 15.

Other embodiments of the probe and other arrangements of the photodiodes, as well as a different number of photodiodes on the measurement plane, are possible.

Figure 4:
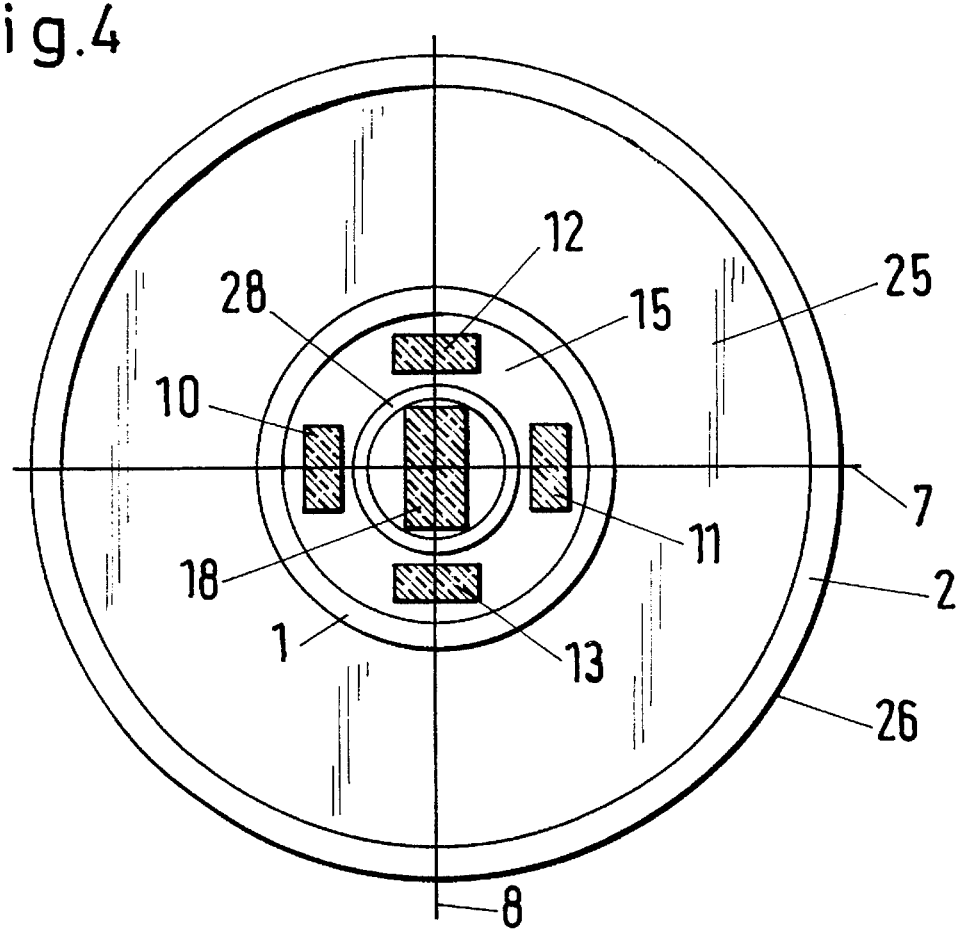
FIG. 4 shows a plan view of the probe of a second embodiment of the inventive probe with an optical reflection measurement portion, comprising four photodiodes and one photodetector, as well as with suction cuff that is shown.
Figure 5:
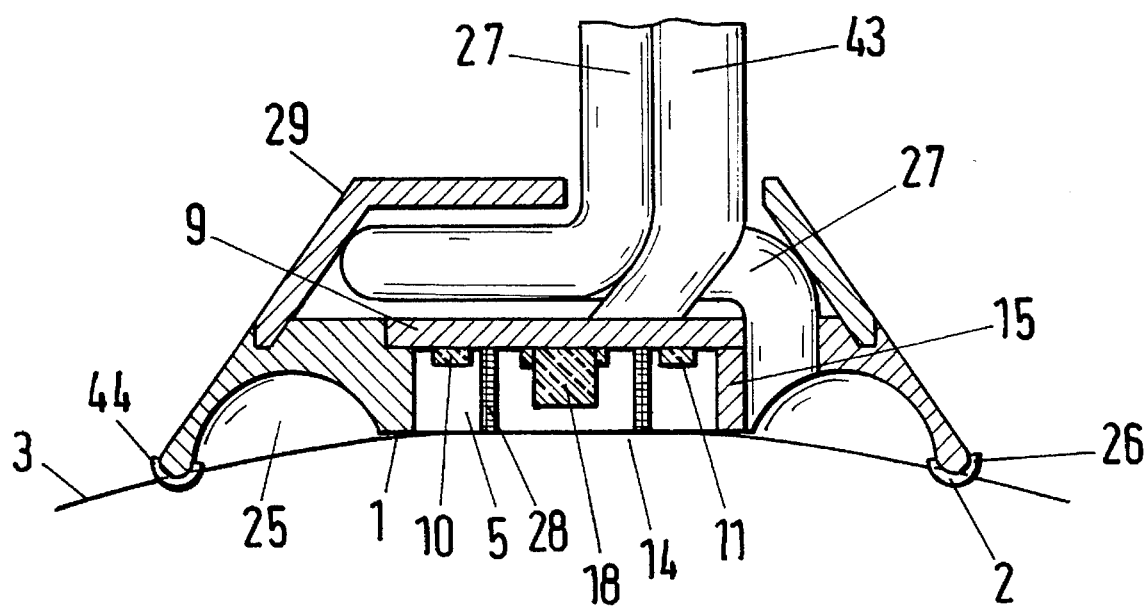
FIG. 5 shows a section A–B through the embodiment shown in FIG. 4.

The ratio of diameter to depth is shown diagrammatically in FIG. 5, which shows a cross section of the probe 15 of FIG. 4. This ratio is not more than 3:1, in order to guarantee that the probe 15 can be placed comfortably and easily on the scalp of the fetus before or during the delivery process. Moreover, due to the small, advantageous diameter-to-depth ratio, a firm hold of the probe is ensured. By these means, the effects of external, mechanical disturbances on the probe during the delivery process are minimized, only as a result of which is an artifact-free measurement possible.

The arrangement shown in FIG. 5 furthermore shows a covering hood 26, which serves as a suction cuff, is assigned to the probe 15 and circularly surrounds it. This covering hood 26 has a semi-cylindrical cavity 25, which lies in the cross section of the probe 15 and is constructed circularly about the probe 15. In this embodiment, the covering hood 26 changes over into the conical covering hood 29. The cavity 25 is closed off from the surroundings and the probe 15 by two circular supporting surfaces 1 and 2. The open, annular area of the semi-cylindrical cavity 25 is assigned to the fetal scalp 3 during the oxygen saturation measurement, while the distal emergence planar surface 14, that is, the region enclosed by the supporting surface 1, is not subjected to a partial vacuum.

The cavity 25 is evacuated over the suction line 27, so that the partial vacuum produced holds the probe 15 reliably at the fetal scalp 3 with the distal emergence planar surface 14 of the probe 15 over the covering hood 26. The oxygen content is thus measured at the measuring site without the interfering effects of a partial vacuum.

In this embodiment with four photodiodes 10, 11, 12, 13, the equalizing outlet 33 also serves the same purpose that has already been described in the first embodiment with two photodiodes 10, 11. The electrical leads of the first embodiment are shown in a simplified fashion in this embodiment as electrical lead 43.

An EKG electrode is constructed as a cylindrical tube 28 or as a component with a different cross sectional shape and different dimensions, which has contact with the fetal scalp 3 and shields the photodetector 18 electrically and optically from the photodiodes 10, 11, 12, 13, so that only light which is reflected from the scalp 3, reaches the photodetector 18. A casing 44, which shields the EKG electrode 28 electrically, is assigned to the circular supporting surface 2. Alternatively, it is possible to do without this casing in other embodiments.

The photodiodes 10, 11, 12, 13, the photodetector 18 and the cylindrical tube 28 thus form an optical reflection measurement portion 5, which is bounded by the common planar element 9, the distal emergence planar surface 14 and the supporting surface 1 of the circular covering hood 26, which is assigned to the probe 15 (FIG. 5).

As already mentioned, the optical reflection measurement portion 5 is divided from the evacuated cavity 25 by the supporting surface 1 and is therefore not subjected to a partial vacuum.

While the foregoing description and drawings represent the preferred embodiments of the present invention, it will be obvious to those skilled in the art that various changes and modifications may be made therein without departing from the true spirit and scope of the present invention.

| List of Reference Symbols | |
|---|---|
| Circular supporting surfaces | (1, 2) |
| Fetal scalp | (3) |
| Optical reflection measurement portion | (5) |
| Axes of symmetry | (7, 8) |
| Common planar element | (9) |
| Photodiodes | (10, 11, 12, 13) |
| Distal emergence planar surface | (14) |
| Probe | (15) |
| Photodetector | (18) |
| Lead connections | (19, 20, 21) |
| Pulsoxymeter | (24) |
| Cavity | (25) |
| Covering hood | (26) |
| Suction line | (27) |
| Cylindrical tube | (28) |
| Conical covering hood | (29) |
| Equalizing outlet | (33) |
| Plug-and-socket connector | (36) |
| Opaque barrier | (40) |
| Covering of equal diameter | (41) |
| Recesses on opposite sides | (42) |
| Electrical connecting lead | (43) |
| Casing | (44) |

What is claimed is:

1. Apparatus for measuring the oxygen saturation of fetuses during childbirth comprising:
 a probe for attachment to a fetal scalp and being held in position by a partial vacuum, said probe having at least two photodiodes operating at different wavelengths and a photodetector forming parts of an optical reflection measurement portion for determining oxygen saturation in the arterial or pulsating bloodstream of fetuses, oxygen saturation being proportional to the ratio of oxyhemoglobin to the sum of oxyhemoglobin and desoxyhemoglobin, said probe providing output signals to an evaluating pulsoxymeter, wherein said optical reflection measurement portion is arranged on a distal emergence planar surface of said probe which itself is not subjected to a partial vacuum.

2. The apparatus of claim 1, wherein said probe is coupled to the evaluating pulsoxymeter by a plug-and-socket connector to allow for sterilization of the probe after use.

3. The apparatus of claim 1, including a covering hood for enclosing the distal emergence planar surface, said hood including a cavity which is approximately semi-cylindrical in cross section, supporting surfaces of the hood being circular lying outside of the distal emergence measurement portion and surrounding the probe circularly.

4. The apparatus of claim 3, wherein an EKG electrode, within a region surrounded by the covering hood and disposed as a cylindrical tube between the photodiodes and the photodetector, is provided for the purpose of electrical and optical shielding.

5. The apparatus of claim 3, wherein a casing is provided to the circular supporting surface for the purpose of electrically shielding an EKG electrode.

6. The apparatus of claim 1, wherein the photodiodes of the optical reflection measurement portion lie on a common planar element together with the photodetector and are disposed mutually opposite to one another on a common axis of symmetry of the probe.

7. The apparatus of claim 1, wherein four photodiodes are disposed circularly about the photodetector on a surface of a common planar element of the probe.

8. The apparatus of claim 1, wherein the probe has a diameter and depth and the ratio of the diameter to the depth of the probe is less than 3:1.

9. The apparatus of claim 1, wherein an equalizing outlet, adapted to being inserted in a lead connection by way of a plug connector, is constructed as an electrical circuit for adjusting the light intensity of the photodiodes relative to one another.

10. The apparatus of claim 1, wherein the probe includes a housing and connection leads, and wherein a junction of the probe housing and connection leads is of conical construction.

11. The apparatus of claim 1, wherein the probe has mutually opposite recesses serving as abutment for jaws of surgical forceps.

* * * * *